June 7, 1966 W. LEE Plant Pat. 2,644
RAPHIOLEPIS PLANT
Filed Aug. 12, 1964
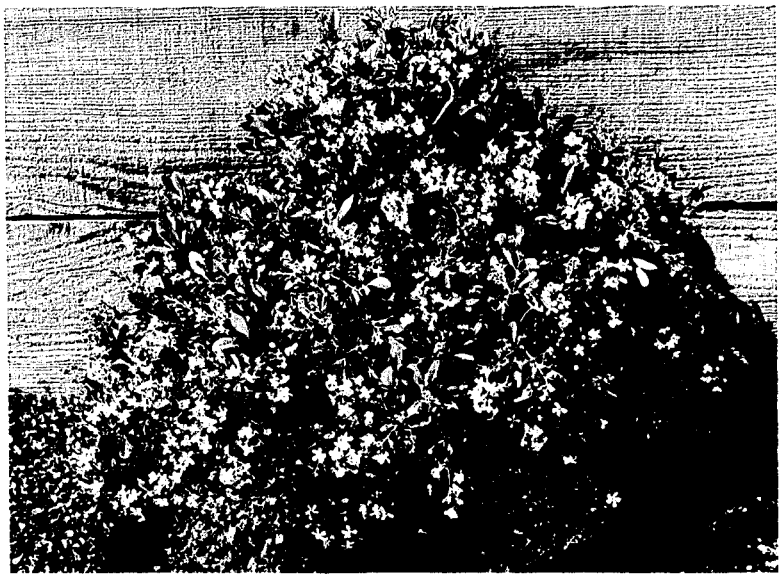
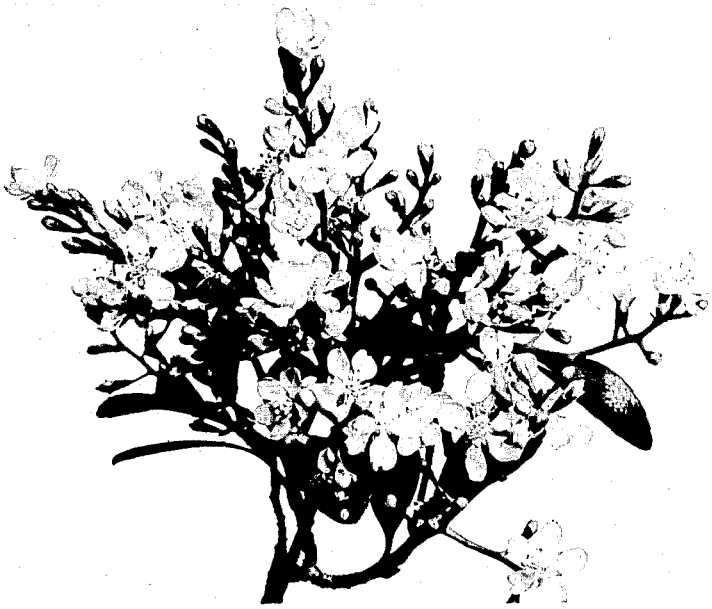
INVENTOR
WALTER LEE
BY J. F. Cuneo
ATTORNEY United States Patent Office Plant Pat. 2,644
Patented June 7, 1966

2,644
RAPHIOLEPIS PLANT

Walter Lee, Bellflower, Calif., assignor to Monrovia Nursery Co., Azusa, Calif., a corporation of California Filed Aug. 12, 1964, Ser. No. 389,231
1 Claim. (Cl. Plt.—54)

This invention relates to a new and distinct variety of Raphiolepis plant, a member of the Rosaceae family.

The plant was discovered by me in 1958, as a chance seedling growing in a bed of *Raphiolepis indica,* a nonpatented variety which has been identified by the trade name of "Springtime," that was being cultivated by me on my property located at 9429 East Linden, Bellflower, California.

The new variety has been asexually reproduced by me on my property in Bellflower, California, primarily by cuttings and graftings. The seed parent of the new variety is an unpatented variety of *Raphiolepis indica* that is widely grown in Southern California, the pollen parent of the new variety is unknown. A large number of plants of the new distinct variety have been reproduced asexually by the methods indicated above, and in all cases the resulting plants have exhibited the distinguishing characteristics of the parent plant showing that the strain is true. The new variety cannot be reproduced true from seed.

My new and distinct variety is characterized as to novelty by its vigorous compact growth which may be best defined as a mounding habit; by its profuse blooming period which extends from April through May and is followed by a lighter blooming period in the fall of the year; and by the color of its blooms. The leaves of the new variety are small, coriaceous with serrulate margins, the shape of the leaf is obovate to oblanceolate.

The new variety differs from its seed parent *Raphiolepis indica* in the smaller size of its leaves, its compact mounding habit of growth, and by the color of its flowers which are Neyron Rose whereas the flowers of the parent plant are light pink in color. The panicles of flowers of the new variety are described as broadly pyramidal in shape while the flowers of the seed parent are narrowly pyramidal.

The claimed variety shows characteristics which, when compared to another nonpatented variety of Raphiolepis that is identified by the trade name of "Enchantress," clearly distinguish it from the variety "Enchantress." The leaves of the new variety are up to two and one-quarter inches in length, measured from the base of the petiole, and are approximately seven-eighths of an inch in width; the leaves of "Enchantress" are much larger, some leaves attain a length of three and one-quarter inches, measured from the base of the petiole and reach a width of one and one-half inches. The petiole of the new variety seldom exceeds three-eighths inch in length while the petiole of the "Enchantress" is five-eighths inch in length.

The blooms of "Enchantress" are Rhodamine Pink 527/1, based on the British Horticultural Colour Charts, which is an entirely different color than Neyron Rose 623, the predominant color of the petals of the new variety. One feature that particularly distinguishes the new variety from "Enchantress" is that the petals of "Enchantress" are uniform in color throughout the entire length of the petal whereas those of the new variety are Neyron Rose 623 at the darkest portion and gradually shade to Neyron Rose 623/1 as the base portion is approached. The base portion of each petal is white, and extends an appreciable distance from the base. The flowers of the claimed variety are appreciably larger than those of "Enchantress."

The accompanying illustrations in full color show the entire plant and an enlarged view of one of the panicles of flowers. The color of the leaves and flowers are as close as can be reproduced by this method of illustration. To facilitate the identification of the important colors, the terminology adapted by the British Horticultural Colour Charts has been adopted.

A detailed description of the new variety follows:

*The plant*

Type: Evergreen bush.
Growth habit: Mounding habit.
Size: The bush reaches a height of approximately two and one-half feet and a width that is four feet or more.
Foliage:
*Quantity.*—Abundant.
*Shape.*—Obovate to oblanceolate. The tip of the leaf is obtuse with the base of the leaf being attenuate.
*Size.*—Mature leaves are from one and one-half to two and one-quarter inches in length and vary in width from three-quarters to seven-eighths of an inch.
*Color.*—The upper portion of the leaf is dark green and the underneath side of the leaf is a lighter shade of green.
*New Foliage.*—New growth has a dull reddish color, subsequently changing to a lighter green than the mature leaves while retaining a dull red margin.
*Margin.*—The leaves are serrulate for about one-half of three-quarters of the length of the margin from the tip.
*Texture.*—Leaves are coriaceous in texture.
*Petiole.*—The petiole is usually three eighths of an inch in length when fully developed.
*Arrangement.*—The leaves are alternate on the stem.

*The flower*

Blooming habit: The plant blooms profusely during the months of April and May. This blooming period is followed by a lighter blooming period in the fall of the year.
Shape of influorescence: The flowers form in a broadly pyramidal terminal panicle. Size of the individual flower: The flowers are approximately three-quarters of an inch in diameter.
Number of petals: Five petals form a flower.
Shape of petals: Petals are obovate.
Color: The flower petals are Neyron Rose 623, with the central portion of the petal shading to Neyron Rose 623/1. The base of the petals is white.
Sepals: There are five sepals which are united and are tinged with red at the tips.
Peduncle: The flowers are attached to short peduncles that are approximately one-quarter of an inch in length. The peduncle is slightly hairy.

I claim:

A new and distinct variety of Raphiolepis plant substantially as herein shown and described, characterized particularly by the distinctive and unique coloring of the flowers which are Neyron Rose, the base portion of the petals being white; by the broadly pyramidal shape of the panicles of flowers; by the smaller size of the leaves; and by its compact mounding growth habit.

References Cited by the Examiner

Monrovia Nursery Co., Whsle. Catalog of 1959–60.

ABRAHAM G. STONE, *Primary Examiner.*
R. E. BAGWELL, *Assistant Examiner.*